United States Patent
Glock et al.

(10) Patent No.: US 6,552,230 B1
(45) Date of Patent: Apr. 22, 2003

(54) METHOD FOR PREPARING 2-NITRO-5-(PHENYLTHIO)-ANILINES

(75) Inventors: Volker Glock, Krefeld (DE); Willi Streicher, Krefeld (DE); Friedrich-Wilhelm Ullrich, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/720,011
(22) PCT Filed: Jun. 21, 1999
(86) PCT No.: PCT/EP99/04296
§ 371 (c)(1),
(2), (4) Date: Dec. 19, 2000
(87) PCT Pub. No.: WO00/01669
PCT Pub. Date: Jan. 13, 2000

(30) Foreign Application Priority Data

Jul. 1, 1998 (DE) .......................................... 198 29 357

(51) Int. Cl.$^7$ .......................................... C07C 323/00
(52) U.S. Cl. .................................................... 564/430
(58) Field of Search .......................................... 564/430

(56) References Cited

U.S. PATENT DOCUMENTS

| | | | | |
|---|---|---|---|---|
| 4,011,320 A | 3/1977 | Beard et al. | ................. | 424/249 |
| 4,034,107 A | 7/1977 | King et al. | .................. | 424/309 |

FOREIGN PATENT DOCUMENTS

| | | |
|---|---|---|
| CA | 1030542 | 5/1978 |
| CA | 1241665 | 9/1988 |
| CH | 619458 | 9/1980 |
| DE | 4202262 | 7/1992 |
| EP | 0061110 | 9/1982 |
| GB | 1460641 | 1/1977 |

OTHER PUBLICATIONS

J. Med. Chem., 18, (month unavailable), 1975, pp. 1164–1166, E. A. Averkin et al.,"Methyl 5(6)–Phenylsulfinyl–2–Benzimidazolecarbamate, A New, Potent Anthelmintic[1]".

Arch. Pharm., 316, (month unavailable) 1983, pp. 638–643, R. Rastogi et al, "Synthesis of 2–Substituted Thiobenzimidazoles as Potential Anthelminthics[1)]".

Chemical Abstracts, vol. 123, Nr. 7, Aug. 14, 1995, Columbus, OH, US, Abstract Nr. 83277C, L. Huang et al, "Drugs Against Hydatidoisis: Synthesis of Metabolites and Analogs of Albendazole", p. 1036, left hand column, & Zhongguo Yiyao Gongye Zazhi (month unavailable), 1995, 26(2), pp. 55–59.

Chemical Abstract, vol. 125, Nr. 5, Jul. 29, 1996, Columbus, OH, US, Abstracts Nr. 58055u, A.

Skibinski et al, "Preparation of Dimethyl Ester of N–(2–((Methoxyacetyl) Amino)–4–(Phenylthio)phenyl) Carbonimidoyl–N, N'–Bis–Carbamic Acid", p. 1107, right hand column, & Pol. J. Appl. Chem, (month unavailable), 1995, 39(1), pp. 91–94 (Eng.).

J. Med. Chem., (month unavailable) 1992, 35, pp. 4455–4463, T. Güngör, "Cardiotonic Agents. Synthesis and Cardiovascular Properties of Novel 2–Arylbenzimidazoles and Azabenzimidazoles".

*Primary Examiner*—Joseph K. McKane
*Assistant Examiner*—Andrea D. Small
(74) *Attorney, Agent, or Firm*—Godfried R. Akorali; Richard E. L. Henderson

(57) ABSTRACT

The invention relates to a process for preparing 2-nitro-5-(phenylthio)anilines of formula (I)

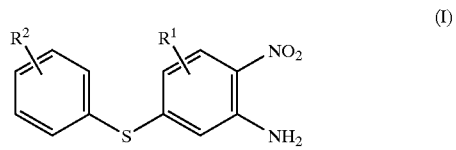

wherein $R^1$ represents hydrogen, $C_1$–$C_8$-alkyl, $C_3$–$C_8$-cycloalkyl, $C_1$–$C_8$-alkoxy, or halogen and $R^2$ represents hydrogen, $C_1$–$C_8$-alkyl, $C_3$–$C_8$-cycloalkyl, $C_1$–$C_8$-alkoxy, halogen, or $C_6$–$C_{10}$-aryl optionally substituted with $C_1$–$C_8$-alkyl, $C_1$–$C_8$-alkoxy, or halogen, by reacting, in a solvent, a 5-chloro-2-nitroaniline of the formula (II)

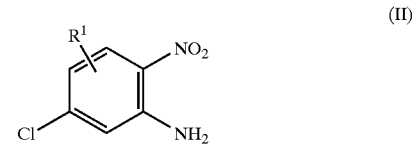

wherein $R^1$ is as defined for formula (I), with a thiophenol of the formula (III)

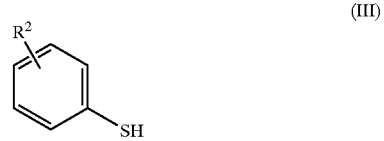

wherein $R^2$ is as defined for formula (I), and ammonia.

9 Claims, No Drawings

METHOD FOR PREPARING 2-NITRO-5-(PHENYLTHIO)-ANILINES

This application is a 371 of PCT/EP99/04296 Jun. 21, 1999.

2-Nitro-5-(phenylthio)-anilines are useful intermediates for preparing herbicides (see EP-A 61 110) for preparing active compounds for the treatment of diseases caused by worms (see DE-A 2 332 398) and for preparing growth-promoting agents for domestic and working animals (see CH-A 619 458).

To prepare 2-nitro-5-(phenylthio)-anilines, 5-chloro-2-nitroanilines can be reacted with thiophenols for example by initially converting the thiophenpol, using an oily emulsion of sodium hydride in dimethylformamide, into the corresponding sodium thiophenolate and converting the latter, by addition of a 5-chloro-2-nitroaniline, into the product which is then precipitated using water (see DE-A 2 406 584).

According to DE-A 2 332 398 and DE-A 2 549 417, thiophenol and 5-chloro-2-nitroanilines were boiled under reflux in dimethylformamide in the presence of potassium carbonate for about 7 hours. After aqueous work-up and recrystallization, the product was obtained in yields of 77 to 88%. Using an almost identical procedure, but a reaction time of only 1 hour at 100° C., a crude yield of 91% was obtained; however, the material still had to be recrystallized in order to achieve the required quality (see J. Med. Chem. 18, 1164 (1975)).

EP-A 61 110 likewise uses potassium carbonate. Here, 2-methyl-6-nitro-3-phenylthio-aniline was prepared in dimethyl sulfoxide at 110° C., in a yield of 92%.

All these processes have the disadvantage that, for product isolation, the reaction mixtures, which comprise dipolar aprotic solvents, have to be subjected to aqueous work-up. This gives rise to waste water which carries a high load of organic solvents and has to be disposed of. Furthermore, the yield and/or the purity of the product obtained is frequently unsatisfactory.

For carrying out the reaction in ethanol under reflux conditions, potassium hydroxide was employed as base (See CH-A 619 458 and Arch. Pharm. 316, 638 (1983)). After cooling of the reaction mixture, the product was filtered off and then recrystallized, likewise giving unsatisfactory yields of from 80 to 83%.

According to DE-A 4 202 262, 5-chloro-2-nitroaniline was prepared with thiophenol in a two-phase system of aqueous sodium hydroxide solution and toluene with participation of tetrabutylammonium bromide, in a yield of 98%. Other phase-transfer catalysts gave poorer yields. This process generates waste water loaded with the phase-transfer catalysts, some of which are toxic, and the waste water is very difficult to purify, owing to the presence of the phase-transfer catalysts.

Accordingly, there is still a need for a process for preparing 2-nitro-5-phenyl-thio-anilines which can be carried out giving good yields, but which does not cause any particular ecological problems.

Accordingly, the present invention provides a process for preparing 2-nitro-5-(phenylthio)-anilines of the formula (I)

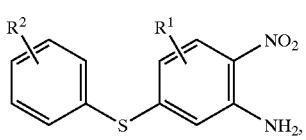

in which
$R^1$ represents hydrogen, $C_1$–$C_8$-alkyl, $C_3$–$C_8$-cycloalkyl, $C_1$–$C_8$-alkoxy or halogen and $R^2$ represents hydrogen, $C_1$–$C_8$-alkyl, $C_3$–$C_8$-cycloalkyl, $C_1$–$C_8$-alkoxy, halogen or optionally $C_1$–$C_8$-alkyl-, $C_1$–$C_8$-alkoxy- or halogen-substituted $C_6$–$C_{10}$-aryl, by reacting 5-chloro-2-nitroanilines of the formula (II)

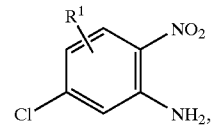

in which
$R^1$ is as defined under formula (I)
with thiophenols of the formula (III)

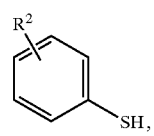

in which
$R^2$ is as defined under formula (I),
characterized in that a 5-chloro-2-nitroaniline of the formula (II) is reacted in a solvent with a thiophenol of the formula (III) and ammonia.

In the formulae (I) and (II), $R^1$ preferably represents hydrogen, $C_1$–$C_4$-alkyl or chorine, particularly preferably hydrogen, methyl or chlorine.

The 5-chloro-2-nitroanilines of the formula (II) and thiophenols of the formula (III) which can be used for the process according to the invention can be obtained in a known manner or analogously thereto, if they are not commercially available.

In a preferred embodiment of the process according to the invention, the 5-chloro-2-nitroaniline is question is prepared by chlorine-amine exchange from the corresponding 2,4-dichloronitrobenzene, using ammonia (see, for example, J. Med. Chem. 35, 4455 (1992) and DE-A 3 431 827)), and the process according to the invention is then carried out without intermediate isolation of the 5-chloro-2-nitroaniline formed, by adding the thiophenol and, if required, additional ammonia, in the same reaction vessel. In principle, the order in which the reactants are added is not critical for the process according to the invention. Preferably, the 5-chloro-2-nitrolaniline of the formula (II), dissolved in a solvent, is mixed with ammonia, and a thiophenol of the formula (III) is then added. The reactants can also be added in any other order. They can also be metered in simultaneously into the reaction mixture.

In the formulae (I) and (III), $R^2$ preferably represents hydrogen or $C_1$–$C_4$-alkyl, particularly preferably hydrogen.

Suitable solvents for the process according to the invention are virtually all customary solvents, for example inorganic solvents, such as water or anhydrous ammonia, and organic solvents, such as alcohols, ethers, hydrocarbons, aromatics, chloroaromatics and dipolar aprotic solvents. Specific examples of organic solvents which may be mentioned are: methanol, ethanol, n-propanol, isopropanol, n-butanol, isobutanol, sec-butanol, tert-butanol, glycol, diethyl ether, methyl tert-butyl ether, tetrahydrofuran, dimethylformamide, N-methylpyrrolidone, toluene and chlorobenzene. Preference is given to nonpolar and low-polarity solvents, such as alcohols, ethers, hydrocarbons, aromatics and chloroaromatics, in particular methanol, isopropanol, isobutanol, toluene and chlorobenzene.

The use of phase-transfer catalysts is not required.

The ammonia used can be of technical grade.

Based on 1 mole of the 5-chloro-2-nitroaniline used, it is possible to employ, for example, from 0.5 to 2 mol, in particular from 1 to 1.2 mol, of a thiophenol and from 1 to 30 mol, in particular from 2 to 15 mol, of ammonia.

The process according to the invention can be carried out, for example, at temperatures in the range from 20 to 140° C. The process is preferably carried out at from 40 to 100° C. During the practice of the process according to the invention pressures in the range from 1 to 20 bar, for example, may be present. The process is preferably carried out at from 3 to 12 bar, in particular under the autogenous pressure that becomes established in a sealed reaction vessel under the reaction conditions used. In particular towards the end of the reaction, it is advantageous to keep the temperature below 80° C. and the pressure below 10 bar.

The process according to the invention can be carried out, for example, by initially charging the 5-chloro-2-nitroaniline of the formula (II) together with the solvent in an autoclave, then heating the mixture to the desired reaction temperature, then adding ammonia and then metering in the thiophenol of the formula (III), for example in the course of from 0.5 to 5 hours. It is advantageous to meter in additional ammonia during the metered addition of the thiophenol, for example such that the pressure which prevailed prior to the metered addition of the thiophenol is maintained, within a range of ±20%. After the metered addition of the thiophenol has ended, the reaction mixture may be stirred for some extra time, for example for from 1 to 20 hours, under the above-mentioned pressure and temperature conditions, in particular at temperatures below 80° C.

The work-up of the reaction mixture which is then present is simple. Frequently, in particular when non-polar or low-polarity solvents are used, a suspension which contains the 2-nitro-5-(phenylthio)-aniline of the formula (I) which has been prepared in solid form is present after cooling of the autoclave. In this case, it is generally sufficient to filter off the reaction mixture and to wash the solid residue, for example with water. If desired, ammonia can be recovered from the ammonium chloride that is formed, by adding a strong base, for example aqueous sodium hydroxide solution. If dipolar aprotic solvents are used, it is advantageous to add water to the reaction mixture prior to the isolation of the product that has been prepared.

The process according to the invention affords 2-nitro-5-(phenylthio)-anilines of the formula (I) generally in yields of more than 88% of theory and purities of more than 90% by weight. Frequently, the yields are above 92% of theory, for example above 95% of theory, and the purities frequently exceed 94% by weight.

It is extremely surprising that, using the process according to the invention, such good results can be obtained in a simple manner, without any particular associated ecological problems, since ammonia itself is a good nucleophile and capable of replacing chlorine bound to aromatic compounds by the amino group. Surprisingly, however, virtually no such reaction occurs with the compounds of the formula (II) used. In contrast, in the process according to the invention, the chlorine which is present in the compounds of the formula (II) is, in an unexpected manner and despite the presence of ammonia, selectively replaced by the thiophenol radical.

The ecology is particularly favourable when nonpolar or low-polarity solvents are used, since only small amounts of these pass over into the waste water. Hitherto, however, the use of dipolar aprotic solvents or the use of phase-transfer catalysts (in combination with low-polarity solvents) has been considered to be indispensable. However, in the presence of phase-transfer catalysts large amounts of dipolar aprotic solvents and low-polarity solvents end up in the waste water.

EXAMPLES

Example 1

In a 1 l steel autoclave, 200 g of 5-chloro-2-nitroaniline (87.3% by weight) were suspended in 200 ml of chlorobenzene. The reaction mixture was then heated to 60° C. and 45.9 g of ammonia were pumped into the autoclave, resulting in a pressure of 4 bar. At this temperature, 123 g of thiophenol (98% by weight) were then pumped into the autoclave over a period of 2 hours. At the same time, the pressure was maintained at a constant 4 bar by further metered addition of ammonia. After 6 hours, the autoclave was cooled and vented. The reaction mixture was mixed with 195 g of aqueous sodium hydroxide solution (23% by weight strength) and heated to 90° C. The phases were then separated at 90° C. The organic phase was cooled to room temperature; it contained 234 g of 2-nitro-5-(phenylthio)-aniline, corresponding to a yield of 92.2% of theory. Recrystallization was not necessary.

Example 2

In an autoclave, 255 g of 5-chloro-2-nitroaniline (78.3% by weight) were suspended in 250 ml of isopropanol. The reaction mixture was heated to 60° C. and 95.7 g of ammonia were pumped into the autoclave, resulting in a pressure of 9 bar. At this temperature, 161 g of thiophenol (98% by weight) were then pumped into the autoclave over the course of 1.5 hours. At the same time, the pressure was maintained at 9 bar by further metered addition of ammonia. After 6 hours, the autoclave was cooled to room temperature and vented. The content of the autoclave was filtered off, the autoclave was rinsed with isopropanol and the liquid used for rinsing was also filtered off. The combined residues were washed with water and dried. This gave 298.6 g of 2-nitro-5-(phenylthio)-aniline in the form of a yellow powder having a content of 91.2% by weight. This corresponds to a yield of 96.4% of theory.

Example 3

In an autoclave, 200 g of 5-chloro-2-nitroaniline (79.2% by weight) were suspended in 200 ml of isobutanol. The reaction mixture was heated to 60° C. and 26 g of ammonia were pumped into the autoclave, resulting in a pressure of 4 bar. At this temperature, 126 g of thiophenol (98% by weight) were then pumped into the autoclave over the course of 1.5 hours. At the same time, the pressure was maintained at 4 bar by further metered addition of ammonia. After 6 hours, the autoclave was cooled to room temperature and vented. The content of the autoclave was filtered off, the autoclave was rinsed with isobutanol and the liquid used for rinsing was also filtered off. The combined residues were washed with water and dried. This gave 240.6 g of 2-nitro-5-(phenylthio)-aniline in the form of a yellow powder having a content of 90.0% by weight. This corresponds to a yield of 95.8% of theory.

Example 4

In an autoclave, 358.8 g of 5-chloro-2-nitroaniline (79.2% by weight) were suspended in 410 ml of toluene. The reaction mixture was heated to 60° C. and 98 g of ammonia were pumped into the autoclave, resulting in a pressure of 9 bar. At this temperature, 253.5 g of thiophenol (98% by weight) were then pumped into the autoclave over the course of 2 hours. At the same time, the pressure was maintained at a constant 9 bar by further metered addition of ammonia. After 6 hours, the autoclave was cooled to room temperature and vented. The reaction mixture contained 384.5 g of 2-nitro-5-(phenylthio)-aniline, corresponding to a yield of 94.8% of theory.

Example 5

Example 4 was repeated, but the solvent used was a corresponding amount of methanol, giving the product in a yield of 97.7% of theory.

Example 6

Example 4 was repeated, but the solvent used was a corresponding amount of dimethylformamide, giving the product, after addition of water, in virtually quantitative reaction yield.

Example 7

Example 4 was repeated, but the solvent used was a corresponding amount of water, giving the product in a reaction yield of 98% of theory.

Example 8

200 ml of isopropanol were initially charged in an autoclave, and 196 g of 2,4-dichloronitrobenzene (98% by weight) were added. The autoclave was sealed and heated to 120° C. At this temperature, ammonia was pumped in until a pressure of 30 bar had been reached. By metered further addition of ammonia during the reaction, the pressure was maintained at 30 bar for the next 12 hours. The reaction mixture was then cooled to 60° C. and 118 g of thiophenol (98% by weight) were then metered in over the course of 2 h. The reaction mixture was then stirred for 6 hours, cooled to room temperature and vented. The product suspension was filtered off with suction and the solid was washed initially with isopropanol and then with water, and dried. This gave 232.2 g of 2-nitro-5-(phenylthio)-aniline having a content of 94.9% by weight, corresponding to a yield of 89.5% of theory.

What is claimed is:

1. A process for preparing a 2-nitro-5-(phenylthio)aniline of formula (I)

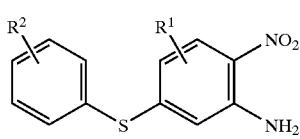

(I)

wherein
  $R^1$ represents hydrogen, $C_1$–$C_8$-alkyl, $C_3$–$C_8$-cycloalkyl, $C_1$–$C_8$-alkoxy, or halogen and
  $R^2$ represents hydrogen, $C_1$–$C_8$-alkyl, $C_3$–$C_8$-cycloalkyl, $C_1$–$C_8$-alkoxy, halogen, or $C_6$–$C_{10}$-aryl optionally substituted with $C_1$–$C_8$-alkyl, $C_1$–$C_8$-alkoxy, or halogen,
comprising (a) reacting a 2,4-dichloronitrobenzene of the formula

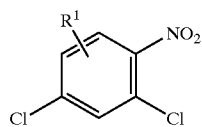

wherein $R^1$ is defined as for formula (I), with ammonia to form a 5-chloro-2-nitroaniline of the formula (II)

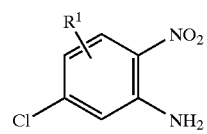

(II)

wherein $R^1$ is as defined for formula (I), (b) reacting the resultant 5-chloro-2-nitroaniline of the formula (II), in the same reaction vessel without intermediate isolation and in a solvent, with
  (i) a thiophenol of the formula (III)

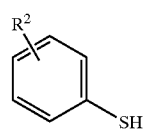

(III)

wherein $R^2$ is as defined for formula (I), and
  (ii) ammonia.

2. A process according to claim 1 wherein $R^1$ represents hydrogen, $C_1$–$C_4$-alkyl, or chlorine and $R^2$ represents hydrogen or $C_1$–$C_4$-alkyl.

3. A process according to claim 1 wherein the solvent in step (b) is water, anhydrous ammonia, an alcohol, an ether, a hydrocarbon, an aromatic, a chloroaromatic, or a dipolar aprotic solvent.

4. A process according to claim 1 wherein from 0.5 to 2 mols of a thiophenol and from 2 to 15 mols of ammonia are employed per 1 mole of the 5-chloro-2-nitroaniline.

5. A process according to claim 1 wherein the temperature in step (b) is in the range from 20 to 140° C.

6. A process according to claim 1 wherein the pressure in step (b) is in the range from 1 to 20 bar.

7. A process according to claim 1 wherein the pressure in step (b) is the autogenous pressure that becomes established in a sealed reaction vessel during the process.

8. A process according to claim 1 wherein the 5-chloro-2-nitroaniline of formula (II) is charged with the solvent in an autoclave, the mixture is then heated to the desired reaction temperature, ammonia is then added, and the thiophenol of the formula (III) is then metered in.

9. A process according to claim 1 wherein the mixture that is present after the reaction has ended is worked up by cooling the mixture, optionally mixing the cooled mixture with water, and filtering off and washing the residue to obtain the 2-nitro-5-(phenylthio)aniline of formula (I).

* * * * *